United States Patent [19]

Rawlings et al.

[11] Patent Number: 5,554,366

[45] Date of Patent: *Sep. 10, 1996

[54] SKIN CARE METHOD AND COMPOSITION

[75] Inventors: Anthony V. Rawlings, Wyckoff, N.J.;
Allan Watkinson, Bedford, Great Britain

[73] Assignee: Elizabeth Arden Co., Division of Conopco, Inc., New York, N.Y.

[*] Notice: The term of this patent shall not extend beyond the expiration date of Pat. No. 5,439,935.

[21] Appl. No.: 375,076

[22] Filed: Jan. 17, 1995

Related U.S. Application Data

[63] Continuation of Ser. No. 40,812, Mar. 31, 1993, abandoned.

[30] Foreign Application Priority Data

Apr. 2, 1992 [GB] United Kingdom .................. 9207288

[51] Int. Cl.⁶ .......................... A61K 38/48; A61K 38/46
[52] U.S. Cl. .................... 424/78.03; 424/94.64; 514/844; 514/845; 514/846; 514/847
[58] Field of Search .................. 424/78.03, 94.64; 514/844, 845, 846, 847

[56] References Cited

U.S. PATENT DOCUMENTS

| | | | |
|---|---|---|---|
| 3,660,566 | 5/1972 | Vinson et al. | 424/95 |
| 5,133,968 | 7/1992 | Nakayama et al. | 424/401 |
| 5,439,935 | 8/1995 | Rawlings et al. | 514/451 |

FOREIGN PATENT DOCUMENTS

| | | |
|---|---|---|
| 0425016 | 5/1991 | European Pat. Off. . |
| 0425018 | 5/1991 | European Pat. Off. . |
| 1171183 | 11/1969 | United Kingdom . |
| 84/02846 | 8/1984 | WIPO . |

OTHER PUBLICATIONS

Lundström, Anita et al., "Cell Shedding from Human Plantar Skin In Vitro: Evidence that Two Different Types of Protein Structures are Degraded by a Chymotrypsin–like Enzyme", Arch. Dermatol. Res. vol. 282 (1990) pp. 234–237.

Lundstrom, Anita et al. "Cell Shedding from Human Plantar Skin In Vitro: Evidence of its Dependence on Endogeneous Proteolysis". vol. 91, No. 4, Oct. 1988, pp. 340–343.

Abstract of JP 61207499.

Abstract of "British Society for Investigative Dermatology Annual Meeting, Birmingham, Sep. 1989", British Journal of Dermatology (1990) 122, pp. 259,289. Society Proceedings.

Lundström, Anita et al. "Stratum Corneum Chymotryptic Enzyme: A Proteinase Which May Be Generally Present in the Stratum Corneum and With a Possible Involvement in Desquamation". Acta Derm Venereol (Stockh) vol. 17, 1991, pp. 471–474.

Egelrud, Torbjörn. "Stratum Corneum Chymotryptic Enzyme: Evidence of its Location in the Stratum Corneum Extracellular Space". Investigative Report, European Journal of Dermatology, vol 2, (1992), pp. 46–49.

Lundström, Anita et al. "Evidence that Cell Shedding from Plantar Stratum Corneum In Vitro Involves Endogenous Proteolysis of the Desmosomal Protein Desmoglein I". The Journal of Investigative Dermatology, vol. 94, No. 2, (1990), pp. 216–220.

Lundström, Anita et al. "Cell Shedding from Human Plantar Skin In Vitro: Evidence that Two Different Types of Protein Structures are Degraded by a Chymotrypsin–like Enzyme". Arch. Dermatol. Res. vol. 282 (1990) pp. 234–237.

Certified Translation of French Application No. 1 548 652, Dec. 06, 1968.

*Primary Examiner*—Gary Geist
*Assistant Examiner*—Dwayne C. Jones
*Attorney, Agent, or Firm*—Rimma Mitelman

[57] ABSTRACT

A composition for topical application to the skin for alleviation or prevention of dry flaky skin condition, dandruff or acne comprising stratum corneum chymotrypsin-like enzyme.

The composition may additionally comprise a second enzyme selected from glycosidases, other proteases, lipases and mixtures thereof.

12 Claims, No Drawings

SKIN CARE METHOD AND COMPOSITION

This is a continuation application of Ser. No. 08/040,812, filed Mar. 31, 1993, now abandoned.

FIELD OF THE INVENTION

The invention relates to alleviation or prevention of dry flaky skin conditions by the topical application of stratum corneum chymotrypsin-like enzyme within a skin care composition. This composition may also be used to alleviate acne or dandruff.

BACKGROUND TO THE INVENTION AND PRIOR ART

In normal, healthy epidermis the continuous production of new stratum corneum is balanced by a well-regulated shedding of corneocytes from the skin surface. Little is known about this desquamation process at the molecular level.

It has been shown by A. Lundström and T. Egelrud (J. Invest Dermatol, (1988) 91 340–343; Arch Dermatol Res (1990) 282 234–237; J. Invest Dermatol (1990) 94 216–220) that cohesion between cells in the stratum corneum is dependant on protein structures. These structures must be degraded before cell dissociation can occur.

Furthermore, evidence has been provided to show that cell dissociation is preceded by a degradation of the extracellular parts of desmosomes. (T. Egelrud (1992) European Journal of Dermatology 2 46–49).

A. Lundström and T. Egelrud have shown that the stratum corneum contains a protease enzyme—stratum corneum chymotrypsin-like enzyme (SCCE) which may be involved in the process of cell dissociation (desquamation): (Acta Derm Venereol (1991) 71 471–474), and that this enzyme may be involved in desmosomal degradation.

There has been much activity by cosmetic companies to solve the problem of being able to provide a skin care composition which is truly effective against dry flaky skin conditions. However until now no solution to this problem has been found.

We have surprisingly discovered that desmosomal structures are present in the uppermost layers of the stratum corneum in dry flaky skin conditions, this is not the case in normal skin. Furthermore, we have been able to substantially solve the problem of dry flaky skin conditions by topical application of a skin care composition comprising stratum corneum chymotrypsin-like enzyme.

DEFINITION OF THE INVENTION

Accordingly the invention provides a composition for topical application to the skin, which alleviates or prevents dry skin conditions comprising stratum corneum chymotrypsin-like enzyme.

Preferably the composition comprises 0.00001 to 50% more preferably 0.001 to 20% and even more preferably 0.1 to 10% by weight of the composition stratum corneum chymotrypsin-like enzyme.

Compositions may also additionally include a second enzyme selected from glycosidases, other proteases, lipases and mixtures thereof. Preferably the composition comprises 0.00001 to 50%, more preferably 0.001 to 20%, even more preferably 0.1 to 10% by weight of the composition of the second enzyme.

When such compositions of the invention comprise:

(a) stratum corneum chymotrypsin-like enzyme; and
(b) a second enzyme selected from glycosidases, other proteases, lipases and mixtures thereof;
the ratio of (a) to (b) is preferably 100:1 to 1:1.
Preferably the second enzyme is a glycosidase.

Without wishing to be bound by theory. We believe that the skin care composition containing SCCE is functioning via the penetration of the topically applied SCCE into the uppermost layers of the stratum corneum, where it then assists in the degradation of the desmosomes abnormally present, thus allowing the cohesive links between the cells to break down and desquamation to occur. The activity of the stratum corneum chymotrypsin-like enzyme may be enhanced by the addition of glycosidases, other proteases, lipases or a mixture thereof to the composition.

Stratum Corneum Chymotrypsin-like Enzyme

Stratum corneum chymotrypsin-like enzyme may be extracted from human or animal skin or callus by high salt solution (eg. 2M NaCl), detergent or solvent extraction, and purified by chromatography or electrophoretic techniques. Recombinant stratum corneum chymotrypsin-like enzyme may also be produced by biotechnological means by the over-expression of its gene in yeast, bacteria, plant or mammalian cells.

Glycosidases

Glycosidases may be isolated from animal, plant, fungal or bacterial sources. Typical enzymes include neuraminidase, mannosidase, galactosidase, glucosidase, N-acetyl glucosaminidase and N-acetyl galactosaminidase. Preferably these may be isolated from plant sources including almonds, green coffee beans, and spinach, or may be obtained commercially.

Other Proteases

Other proteases may be isolated from animal, plant, fungal or bacterial sources. Suitable enzymes include bromelain, papain, chymotrypsin & chymotrypsin-like enzymes, cathepsin and cathepsin-like enzymes, alcalase, savinase, chymopapain, clostripain, endoproteinase Asp N, protease V.8, proteinase K, subtilisin, thermolysin, plasmin, pronase, and trypsin & trypsin-like enzyme. Preferably the protease may be isolated from plant sources including the seeds of wheat, barley, maize, oilseed rape, cocoa, linseed, illipe, shea nut, palm kernal, jojoba bean, pea, green bean, broad bean, soya bean and sunflower, and olives, papaya, pineapple, coconut, tomato and figs.

Lipases

Lipases, or similar lipid modifying enzymes, may be isolated from plant, animal or bacterial sources. Suitable enzymes include lipolase, pancreatic lipases, phospholipases, ceramidase, aryl sulphatase, cholesterol esterase, candida rugosa OF360 lipase, humicola sp. lipase, pseudomonas sp. lipase and Candida antarctica A & B lipases.

The Vehicle

The composition according to the invention also comprises a vehicle to act as a dilutant, dispersant or carrier for the active ingredients in the composition, so as to facilitate their distribution when the composition is applied to the skin and/or hair. Preferably the vehicle is cosmetically acceptable.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone ,oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitatic acid, isopropyl linoleate, lauryl lactate, myristyl lactate, decyl oleate, myristyl myristate;

Propellants, such as air, propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The vehicle will usually form from 10 to 99.9%, preferably from 50 to 99% by weight of the emulsion, and can, in the absence of other adjuncts, form the balance of the composition.

Optional Skin benefit Materials and cosmetic Adjuncts

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

Oil or Oily Material

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and nonvolatile, such as polydimethyl siloxanes.

The oil or oily material, when present for the purposes for forming an emulsion, will normally form up to 90%, preferably from 10 to 80% by volume of the composition.

Emulsifier

The composition according to the invention can also optionally comprise one or more emulsifiers the choice of which will normally determine whether a water-in-oil or an oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set out below in Table 1 in which the chemical name of the emulsifiers is given together with an example of a trade name as commercially available, and the average HLB value.

TABLE 1

| Chemical Name of Emulsifier | Trade Name | HLB Value |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |

TABLE 1-continued

| Chemical Name of Emulsifier | Trade Name | HLB Value |
|---|---|---|
| Polyoxyethylene (20) sorbitan monostearate | Tween | 14.9 |
| Polyoxyethylene 20 sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

Water

The composition of the invention can also comprise water, usually up to 80%, preferably from 5 to 80% by volume.

Silicone Surfactant

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

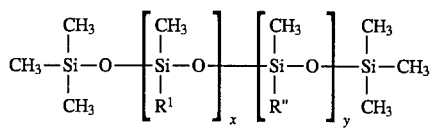

where the groups R' and R" are each chosen from —H, $C_{1-18}$ alkyl and

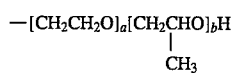

a has a value of from 9 to 115,
b has a value of from 0 to 50,
x has a value of from 133 to 673,
y has a value of from 25 to 0.25.

Preferably, the dimethyl polysiloxane polymer is one in which:
a has a value of from 10 to 114
b has a value of from 0 to 49
x has a value of from 388 to 402
y has a value of from 15 to 0.75
one of groups R' and R" being lauryl, and the other having a molecular weight of from 1000 to 5000.

A particularly preferred dimethyl polysiloxane polymer is one in which:
a has the value 14
b has the value 13
x has the value 249
y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Other Adjuncts

Examples of conventional adjuncts which can optionally be employed include preservatives, such as para-hydroxy benzoate esters; antioxidants, such butyl hydroxy toluene; humectants, such as glycerol, sorbitol, 2-pyrrolidone-5-carboxylate, dibutylphthalate, gelatin, polyethylene glycol, preferably PEG 200–600; buffers, such as lactic acid together with a base such as triethanolamine or sodium hydroxide; surfactants, such as glycerol ethers, ceramides of synthetic, animal or plant origin; waxes, such as beeswax, ozokerite wax, paraffin wax; plant extracts, such as Aloe vera, cornflower, witch hazel, elderflower, cucumber; thickeners; activity enhancers; colourants; perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane, and mixtures thereof.

Since stratum corneum chymotrypsin enzyme is inhibited by zinc ions, metal chelators such as EDTA may be optionally included in the composition to increase activity/decrease inhibition.

USE OF THE COMPOSITION

The composition according to the invention is intended primarily as a product for topical application to human skin, for treating dry flaky skin and to enhance the quality of skin. The composition may also be used to alleviate acne and dandruff.

In use, a small quantity of the composition, for example from 1 to 5 ml, is applied to areas of the skin or hair, from a suitable container or applicator and, if necessary, it is then spread over and/or rubbed into the skin or scalp using the hand or fingers or a suitable device.

PRODUCT FORM AND PACKAGING

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The composition may be used for general lotions and creams, leave-on-creams, wash-off cleansers, face masks shampoos and bath oils.

The invention accordingly also provides a closed container containing a cosmetically acceptable composition as herein defined.

EXAMPLES

In Vitro Assay To Screen For Desmosome Digestion Activity

Stratum corneum cells with desmosomes still attached were obtained by tape stripping human or animal skin. To release the cells from the tape the whole tape was placed into hexane and the cells were collected by centrifugation after which the hexane was aspirated. Alternatively, human plantar stratum corneum, a tissue rich in desmosomes, was ground in liquid nitrogen and dried. The cells were then dispersed into buffer containing a high salt stratum corneum chymotrypsin enzyme extract from pig stratum corneum, in the presence or absence of specific inhibitors to verify enzyme activity. To ascertain the effect of glycosidases, some corneocyte aliquots were treated with a mixture of almond meal extract and neuramidase prior to incubation with the SCCE extract.

Desmosome digestion can then be followed microscopically by examining cell dissociation using an optical microscope. When enzymes fail to digest the desmosomes the cells remain attached to each other. Thus, counting the number of dispersed cells or measuring the dispersed cell mass using a protein assay can be used as a measure of enzyme efficiency. To ensure enzymes were specifically degrading desmosomes, the specific desmosomal digestion by the enzyme was demonstrated as follows:

The desmosomal protein, desmoglein, (dgl) was isolated from the squames by extraction in a urea/SDS/β-mercaptoethanol buffer with subsequent purification of the dgl glycoprotein using concavalin A affinity chromatography. The concavalin A eluate was fractionated by sodium dodecyl sulphate polyacrylamide gel electrophoresis and electrophoretically transferred to PDVF membrane for immunoblotting. The dgl was identified using a specific antiserum with low levels of the antigen being indicative of desmosomal digestion. Results obtained using this methodology are shown in Table 1.

This methodology allows the screening of enzymes prior to testing the most efficacious enzymes in vivo on human skin.

TABLE 1

| Treatment | dgl Levels |
| --- | --- |
| Control | 100% |
| SCCE extract | 13.9% |
| SCCE extract + 100 μM Chymostatin | 51.8% |
| SCCE extract + 1 mM ZnSO$_4$ | 74.6% |
| SCCE extract + 10 μM Aprotinin | 101.7% |
| Glycosidase pretreatment + SCCE extract | 10.1% |

The following examples are to illustrate compositions for topical application embodying the present invention.

| | % w/w |
| --- | --- |
| A Typical Oil-In-Water Cream | |
| SCCE | 0.5 |
| Glycosidases | 0.5 |
| mineral oil | 4.0 |
| Cetyl alcohol POE | 4.0 |
| Cetyl alcohol | 4.0 |
| Triethanolamine | 0.75 |
| Butane 1, 3 diol | 3.0 |
| Xanthum gum | 0.3 |
| Preservative | 0.4 |
| Perfume | qs |
| Butylated hydroxytoluene | 0.01 |
| Water | to 100 |
| A Typical Lotion | |
| SCCE | 1.0 |
| Ethanol | 10.0 |
| Perfume | qs |
| Butylated hydroxytoluene | 0.01 |
| Water | to 100 |
| Water In Oil Emulsion | |
| Fully hydrogenated coconut oil | 3.9 |
| SCCE | 0.5 |
| Glycosidase | 0.5 |
| Polyoxyethylene oleyl ether | 5.0 |
| Bentone 38 | 0.5 |
| Preservative | 0.3 |
| MgSO$_4$ 7H$_2$O | 0.3 |
| Butylated hydroxytoluene | 0.01 |
| Perfume | qs |
| Water | to 100 |

We claim:

1. A composition for topical application to the skin which alleviates or prevents dry flaky skin conditions comprising stratum corneum chymotrypsin-like enzyme 2. A composition according to claim 1 wherein the composition comprises 0.00001 to 50% by weight of the composition stratum corneum chymotrypsin-like enzyme.

3. A composition according to claim 1 wherein the composition comprises 0.001 to 20% by weight of the composition stratum corneum chymotrypsin-like enzyme.

4. A composition according to claim 1 wherein the composition comprises 0.1 to 10% by weight of the composition stratum corneum chymotrypsin-like enzyme.

5. A composition according to claim 1 wherein the composition additionally comprises a second enzyme selected from glycosidases, lipases and mixtures thereof.

6. A composition according to claim 5 wherein the composition comprises 0.00001 to 50% by weight of the composition of the second enzyme.

7. A composition according to claim 5 wherein the second enzyme is a glycosidase.

8. A composition according to claim 1 wherein the composition comprises:

(a) stratum corneum chymotrypsin-like enzyme; and (b) a second enzyme selected from glycosidases, lipases and mixtures thereof;

wherein the ratio of (a) to (b) is 100:1 to 1:1.

9. A composition according to claim 1 wherein the composition further comprises a cosmetically acceptable vehicle for the enzyme.

10. A composition according to claim 1 wherein the composition additionally comprises a protease selected from the group consisting of bromelain, papain, chymotrypsin and chymotrypsin-like enzymes, cathepsin and cathepsin-like enzymes, alcalase, savinase, chymopapain, clostripain, endoproteinase Asp N, protease V.8, proteinase K, subtilisin, thermolysin, plasmin, pronase, and trypsin and trypsin-like enzyme.

11. A composition according to claim 1 wherein the composition comprises:

(a) stratum corneum chymotrypsin-like enzyme; and (b) a protease selected from the group consisting of bromelain, papain, chymotrypsin and chymotrypsin-like enzymes, cathepsin and cathepsin-like enzymes, alcalase, savinase, chymopapain, clostripain, endoproteinase Asp N, protease V.8, proteinase K, subtilisin, thermolysin, plasmin, pronase, and trypsin and trypsin-like enzyme;

wherein the ratio of a:b is from 100:1 to 1:1.

12. A method of relieving or ameliorating dry skin conditions, acne and dandruff which includes the topical application to the skin of a composition comprising stratum corneum chymotrypsin-like enzyme.

* * * * *